United States Patent
Uchegbu et al.

(10) Patent No.: US 10,987,304 B2
(45) Date of Patent: Apr. 27, 2021

(54) OCULAR DELIVERY OF DRUGS

(71) Applicant: Nanomerics Ltd., St. Albans (GB)

(72) Inventors: Ijeoma Uchegbu, St. Albans (GB); Andreas Schatzlein, St. Albans (GB); Lorenzo Capretto, London (GB)

(73) Assignee: Nanomerics Ltd., St. Albans (GB)

( * ) Notice: Subject to any disclaimer, the term of this patent is extended or adjusted under 35 U.S.C. 154(b) by 0 days.

(21) Appl. No.: 15/524,079

(22) PCT Filed: Nov. 2, 2015

(86) PCT No.: PCT/GB2015/053291
§ 371 (c)(1),
(2) Date: May 3, 2017

(87) PCT Pub. No.: WO2016/071677
PCT Pub. Date: May 12, 2016

(65) Prior Publication Data
US 2017/0326064 A1    Nov. 16, 2017

(30) Foreign Application Priority Data
Nov. 3, 2014 (GB) .................................. 1419540.8

(51) Int. Cl.
| A61K 9/00 | (2006.01) |
| A61K 9/08 | (2006.01) |
| A61K 38/13 | (2006.01) |
| A61K 47/36 | (2006.01) |

(52) U.S. Cl.
CPC .............. *A61K 9/0048* (2013.01); *A61K 9/08* (2013.01); *A61K 38/13* (2013.01); *A61K 47/36* (2013.01)

(58) Field of Classification Search
CPC ........ A61K 9/0048; A61K 9/08; A61K 38/13; A61K 47/36
USPC ....................................................... 514/54
See application file for complete search history.

(56) References Cited

U.S. PATENT DOCUMENTS

| 6,395,756 B2 * | 5/2002 | Trimming ............ A61K 9/0048 514/324 |
| 6,468,548 B1 * | 10/2002 | Kis ...................... A61K 9/0048 424/400 |
| 2010/0159014 A1 | 6/2010 | Uchegbu et al. |

FOREIGN PATENT DOCUMENTS

| WO | WO-2004/026912 A1 | 4/2004 | |
| WO | WO 2008/017839 A1 * | 2/2008 | ............ C08B 37/08 |
| WO | WO-2008/017839 A1 | 2/2008 | |

OTHER PUBLICATIONS

Narayanan, S., Review of Optometry, Feb. 7, 2011, pp. 1-6.*
Laupacis et al, CMA Journal, May 1, 1982, 126, 1041-1046.*
Siew et al, Molecular Pharmaceutics, 2012, 9, 14-28, published online Nov. 2, 2011.*
Daull, Philippe et al., Distribution of Cyclosporine A in Ocular Tissues After Topical Administration of Cyclosporine A Cationic Emulsions to Pigmented Rabbits, Cornea, Mar. 2013, 32(3):345-354, Lippincott Williams & Wilkins.
Kuwano, Mitsuaki et al., Cyclosporine A Formulation Affects Its Ocular Distribution in Rabbits, Pharmaceutical Research, Jan. 2002, 19(1):108-111, Plenum Publishing Corporation.
Calvo, Pilar et al., Study of the mechanism of interaction of poly(ε-caprolactone) nanocapsules with the cornea by confocal laser scanning microscopy, International Journal of Pharmaceutics, 1994, 103:283-291, Elsevier Science.
Cheng, Woei Ping et al., Polyelectrolyte Nanoparticles with High Drug Loading Enhance the Oral Uptake of Hydrophobic Compounds, Biomacromolecules, Apr. 5, 2006, 7(5):1509-1520, American Chemical Society.
Qu, Xioazhong et al., Carbohydrate-Based Micelle Clusters Which Enhance Hydrophobic Drug Bioavailability by Up to 1 Order of Magnitude, Biomacromolecules, Nov. 7, 2006, 7(12):3452-3459, American Chemical Society.
Zhao, Xiao-Liang et al., Chitosan micelles as a carrier of cyclosporin A for ocular drug delivery, Journal of China Pharmaceutical University, Apr. 9, 2012, 43(5):418-423.
Siew, Adeline et al., Enhanced Oral Absorption of Hydrophobic and Hydrophilic Drugs Using Quaternary Ammonium Palmitoyl Glycol Chitosan Nanoparticles, Molecular Pharmaceutics, 2012, 9:14-28, American Chemical Society.
Uchegbu, Ijeoma F. et al., Chitosan amphiphiles provide new drug delivery opportunities, Polymer International, Mar. 6, 2014, 63(7):1145-1153, Society of Chemical Industry, wileyonlinelibrary.com.

(Continued)

*Primary Examiner* — Ganapathy Krishnan
(74) *Attorney, Agent, or Firm* — Meunier Carlin & Curfman LLC

(57) ABSTRACT

The present invention relates to an aqueous composition comprising a macrolide immunosuppressant drug at a concentration of less than 2% w/v and an amphiphilic carbohydrate compound having a molecular weight in the range 1-50 kDa, for use in treatment of an eye disorder by topical application to the eye, wherein the amphiphilic carbohydrate compound is present at a concentration below 10% w/v of the composition. A preferred carbohydrate compound is quaternary ammonium palmitoyl glycol chitosan (GCPQ). Pharmaceutical compositions and methods of treatment are also provided. The treatment may be for instance dry eye syndromes (DES), vernal keratoconjunctivitis (VKC), eczema, atopic keratoconjunctivitis (AKC), Sjögren syndrome, post-operative refractive surgery, corneal transplant or contact lens intolerance.

20 Claims, No Drawings

(56) References Cited

OTHER PUBLICATIONS

Amit, Chaudhary et al., Development and Evaluation of Mucoadhesive Microspheres of Levofloxacin Hydrochloride, Journal of Drug Delivery & Therapeutics, Nov. 15, 2012, 2(6):21-24, JDDT, http://jddtonline.info.
International Search Report in International Application No. PCT/GB2015/053291, filed Nov. 2, 2015.
Molpeceres, J. et al., "Exothermic-endothermic heat of solution shift of cyclosporine A related to poloxamer 188 behavior in aqueous solutions", *International Journal of Pharmaceutics*, 1996, 130:75-81, Elsevier Science B.V.
Office Action dated Nov. 1, 2019 in Chinese Application No. 201580072370.9, along with its English translation.
Second Office Action in connection to Chinese Patent Application No. 2015800723709 dated Aug. 4, 2020.
Ebihara et al., Blood Level of Tacrolimus in Patients with Severe Allergic Conjunctivitis Treated by 0.1% Tacrolimus Ophthalmic Suspension, Allergology International vol. 61, No. 2, 2012. www.jsaweb.jp.
Fujita, et al., Pharmacokinetics and Tissue Distribution of Tacrolimus (FK506) After a Single or Repeated Ocular Instillation in Rabbits, Journal of Ocular Pharmacology and Therapeutics, vol. 24, No. 3, 2008.

\* cited by examiner

OCULAR DELIVERY OF DRUGS

CROSS-REFERENCE TO RELATED APPLICATIONS

This application is the U.S. national stage application of International Patent Application No. PCT/GB2015/053291, filed Nov. 2, 2015, which claims priority to United Kingdom Application No. 1419540.8, filed Nov. 3, 2014, the disclosures of each of which are incorporated herein by reference in their entirety.

FIELD OF THE INVENTION

The present invention relates to a new system for the ocular delivery of drugs.

BACKGROUND TO THE INVENTION

Topical ophthalmic formulations are generally used to treat diseases affecting the anterior portion of the eye including but not limited to glaucoma, iritis, conjunctivitis eye infection and dry-eye syndrome (DES). DES refers to a spectrum of ocular surface disorders having various aetiologies and is characterized by chronic eye dryness of the cornea and conjunctiva caused by the improper balance of tear production and drainage or an abnormality in the tear composition. In addition, inflammation of the ocular surface often occurs.

A T-cell lymphocytes mediated inflammatory response has been recognized as a possible cause for DES. As a result, the use of Cyclosporine (CSA) and Tacrolimus (TAC) as topical immunosuppressants have emerged in recent years for the treatment of DES. Such treatments have been shown to decrease inflammatory response and have also been suggested to increase tear production. Due to the hydrophobicity and low aqueous solubility of CSA and TAC, they are generally formulated using oily vehicles which have been linked with bioavailability limitations, stability and ocular tolerance issues.

Emulsion-based formulations, such as the commercially available RESTASIS®, have been shown to provide significant improvement in tear production. However, it is known that RESTASIS® is not optimal and the formulation suffers from low ocular bioavailability. It has been reported that castor oil-based emulsions such as RESTASIS® are characterized by bimodal droplet size distribution. As a result, these compositions are prone to droplet coalescence which limit their shelf life.

Due to the limited pre-corneal residence time of castor oil emulsion droplets, and to the greater affinity of CSA for the oil droplet, a twice-daily administration is required to keep the drug above its therapeutic level in ocular tissues (50-300 ng/g). The use of a positively charged emulsion has been proposed to prolong the residence time on the surface of the cornea. It has been hypothesised that the positive charge on the droplets would increase their interaction with the negatively charged surfaces of corneal cells. In this regard, a positively charged emulsion has shown a higher maximum concentration in the cornea of rabbits, after a single dose, when compared with RESTASIS®. (P. Daull, et al; Distribution of cyclosporine A in ocular tissues after topical administration of cyclosporine A cationic emulsions to pigmented rabbits, Cornea, 32 (2013) 345-354).

Kuwano et al. in Pharmaceutical research, 19 (2002) 108-111 have produced an aqueous dispersion of CSA containing Polyoxyl 40 stearate. The aqueous dispersion of CSA containing Polyoxyl 40 stearate had a higher bioavailability when compared with both castor oil solution of CSA and castor oil o/w emulsion of CSA. The authors suggested that the bioavailability of CSA was affected by its rate of release from its carrier to the dispersion medium. In this respect, the release of CSA from the oily vehicles (castor oil emulsion or solution) was limited by the high partition coefficient of CSA in the oily phase. The composition containing the Polyoxyl 40 stearate did not suffer this impediment as it was aqueous based (devoid of oil). In addition, Polyoxyl 40 stearate formed micelles of 200 nm, which were much smaller than the emulsion droplets; therefore much more CSA could be released.

Calvo et al. in International Journal of Pharmaceutics, 103 (1994) 283-291 reported that the use of $\epsilon$-caprolactone nanoparticles improved the ocular penetration of CSA. The authors demonstrated that these nanoparticles achieve corneal levels of CSA that were five times higher that CSA oily solution. It has been proposed that such enhancement was due to a prolonged residence time of the nanoparticles at the administration site.

WO2004/026912 describes polysaccharides which are used to solubilise hydrophobic drugs. The polysaccharides are amphiphilic and are generally selected from any derivatives of the following: chitosans, dextrans, alginic acids, starches, dextran and guar gums. Quaternary ammonium palmitoyl glycol chitosan (GCPQ) and quaternary ammonium hexadecyl glycol chitosan (GCHQ) are used in the Examples of this patent application as solubilising polysaccharides.

WO2008/017839 describes micellar clusters formed from amphiphilic carbohydrate polymers and their use in formulating hydrophobic drugs. GCPQ is specifically exemplified as an amphiphilic carbohydrate polymer. The use of prednisolone as an immunosuppressant is specifically mentioned.

Although RESTASIS® is currently used to treat DES, there is still need for alternative formulations to treat this problem. Ideal formulations should have stability and ocular tolerability at least comparable to that of RESTASIS® while improving the bioavailability of the drug.

SUMMARY OF THE INVENTION

In accordance with a first aspect of the invention there is provided an aqueous composition comprising a macrolide immunosuppressant drug at a concentration of less than 2% w/v and an amphiphilic carbohydrate compound having a molecular weight in the range 1-50 kDa, for use in treatment of an eye disorder by topical application to the eye, wherein the amphiphilic carbohydrate compound is present at a concentration below 10% w/v of the composition, and is represented by the general formula:

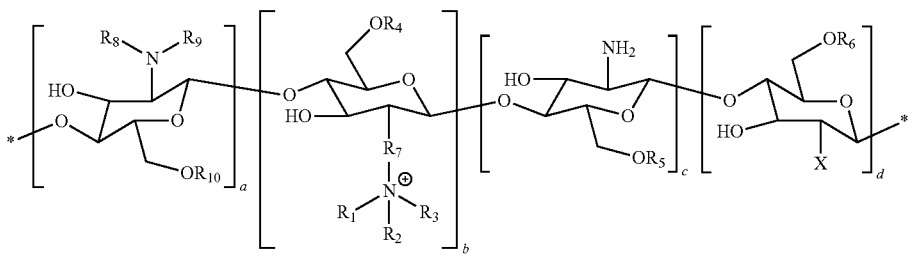

wherein a+b+c+d=1.000 and
a is between 0.00 and 0.84
b is between 0.01 and 0.40,
c is between 0.10 and 0.94, and
d is between 0.05 and 0.50;
and wherein:
X is a hydrophobic group;
$R_1$, $R_2$ and $R_3$ are independently selected from a substituted or unsubstituted alkyl group;
$R_4$, $R_5$, $R_6$ and $R_{10}$ are independently selected from hydrogen, a substituted or unsubstituted alkyl group, a substituted or unsubstituted ether group, or a substituted or unsubstituted alkene group;
$R_7$ may be present or absent and, when present, is an unsubstituted or substituted alkyl group, an unsubstituted or substituted amine group or a substituted or unsubstituted amide group;
$R_8$ and $R_9$ are independently selected from hydrogen and either a substituted or unsubstituted alkyl group, a substituted or unsubstituted ether group, or a substituted or unsubstituted alkene group;
or a salt thereof.

In accordance with a second aspect of the invention there is provided a pharmaceutical composition suitable for ocular administration comprising one or more pharmaceutically acceptable excipients and a macrolide immunosuppressant drug at a concentration of less than 2% w/v and an amphiphilic carbohydrate compound having a molecular weight in the range 1-50 kDa, wherein
the amphiphilic carbohydrate compound is present at a concentration below 10% w/v of the composition, and is represented by the general formula:

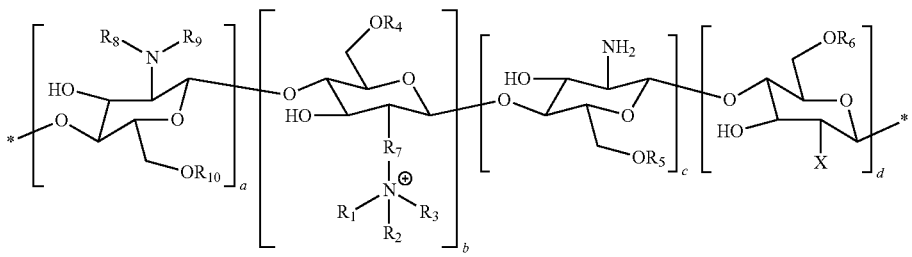

wherein a+b+c+d=1.000 and
a is between 0.00 and 0.84
b is between 0.01 and 0.40,
c is between 0.10 and 0.94, and
d is between 0.05 and 0.50;
and wherein:
X is a hydrophobic group;
$R_1$, $R_2$ and $R_3$ are independently selected from a substituted or unsubstituted alkyl group;
$R_4$, $R_5$, $R_6$ and $R_{10}$ are independently selected from hydrogen, a substituted or unsubstituted alkyl group, a substituted or unsubstituted ether group, or a substituted or unsubstituted alkene group;
$R_7$ may be present or absent and, when present, is an unsubstituted or substituted alkyl group, an unsubstituted or substituted amine group or a substituted or unsubstituted amide group;
$R_8$ and $R_9$ are independently selected from hydrogen and either a substituted or unsubstituted alkyl group, a substituted or unsubstituted ether group, or a substituted or unsubstituted alkene group;
or a salt thereof.

In accordance with a third aspect of the invention there is provided a method of treatment of an eye disorder wherein a composition according to the first or second aspect of the invention is topically administered to the eye.

The amphiphilic carbohydrate compound is capable of self-assembly into nanoparticles in aqueous media.

It is the aim of this invention to provide ophthalmic compositions having good stability, tolerability and bioavailability properties. This is achieved through the use of positively charged amphiphilic self-assembling polymers which are capable of self-assembling in aqueous media. These polymers have multifunctional properties which make them suitable for ophthalmic compositions. They form viscous or non-viscous aqueous dispersions in the form of positively charged nanoparticulate drug carriers which possess muco-adhesive properties. The simplicity of the formulation is maintained as just one excipient can be used. Notably, the use of lipids or emulsions is not required.

The molecular weight of the polymer molecules is important, as below 1 kDa they will generally be too small to encapsulate sufficient levels of drug, and above 50 kDa, the polymer may result in a composition which is too viscous. An appropriate polymer concentration is also important, and should be below 10% w/v of the composition, to prevent gel formation. Furthermore, having a drug concentration below 2% w/v enables complete incorporation within the polymer molecules.

DETAILED DESCRIPTION OF THE INVENTION

The macrolide drug is useful as an immunosuppressant and is typically selected from sirolimus, cyclosporine A, tacrolimus and everolimus, and is preferably cyclosporine A (CSA). CSA is a potent immunosuppressant that has shown potential applications in ophthalmology for the treatment of corneal graft rejection and various eye disorders including keratoconjunctivitis sicca and uveitis. Due to its poor water solubility, CSA is currently formulated as an ophthalmic emulsion (Restasis®), as discussed further above.

The composition of the invention can be used in the treatment of a dry eye syndromes (DES) (also known as keratoconjunctivitis sicca (KCS)), vernal keratoconjunctivitis (VKC), eczema, atopic keratoconjunctivitis (AKC), Sjögren syndrome, post-operative refractive surgery, corneal transplant or contact lens intolerance.

The drug is typically encapsulated by the self-assembled positively charged amphiphilic polymers.

The drug is preferably delivered to the superficial eye tissues such as the cornea and conjunctiva.

The amphiphilic compound is a chitosan derivative.

The amphiphilic carbohydrate compound is represented by the formula:

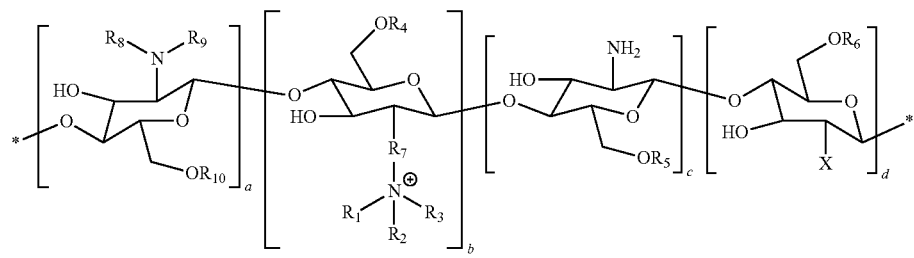

wherein a+b+c+d=1.000 and
a is between 0.00 and 0.84
b is between 0.01 and 0.40,
c is between 0.10 and 0.94, and
d is between 0.05 and 0.50;
and wherein:
X is a hydrophobic group;
$R_1$, $R_2$ and $R_3$ are independently selected from a substituted or unsubstituted alkyl group;
$R_4$, $R_5$, $R_6$ and $R_{10}$ are independently selected from hydrogen, a substituted or unsubstituted alkyl group, a substituted or unsubstituted ether group, or a substituted or unsubstituted alkene group;
$R_7$ may be present or absent and, when present, is an unsubstituted or substituted alkyl group, an unsubstituted or substituted amine group or a substituted or unsubstituted amide group;
$R_8$ and $R_9$ are independently selected from hydrogen and either a substituted or unsubstituted alkyl group, a substituted or unsubstituted ether group, or a substituted or unsubstituted alkene group;
or a salt thereof.

In the above general formula, the a, b, c and d units may be arranged in any order and may be ordered, partially ordered or random. The * in the formula is used to indicate the continuing polymer chain.

In preferred embodiments, the molar proportion of the d units is in the range 0.08-0.25.

Preferably, the molar proportion of the b unit is between 0.02 and 0.4.

As can be seen from the above formula, the a and c units may optionally be absent. The d units provide the first portion of the monomer units that are derivatised with a hydrophobic group, and the b units provide the second portion of the monomer units and are derivatised with a quaternary nitrogen group. When present, the a units provide the third group of monomer units in which the amine groups are derivatised in a different manner to the first or second group.

When present the c units provide the fourth group of monomer units in which the amine groups are underivatised.

In the present invention, the hydrophobic group X is preferably selected from a substituted or unsubstituted group which is an alkyl group such as a $C_{4-30}$ alkyl group, an alkenyl group such as a $C_{4-30}$ alkenyl group, an alkynyl group such as a $C_{4-30}$ alkynyl group, an aryl group such as a $C_{5-20}$ aryl group, a multicyclic hydrophobic group with more than one $C_4$-$C_8$ ring structure such as a sterol (e.g. cholesterol), a multicyclic hydrophobic group with more than one $C_4$-$C_8$ heteroatom ring structure, a polyoxa $C_1$-$C_4$ alkylene group such as polyoxa butylene polymer, or a hydrophobic polymeric substituent such as a poly (lactic acid) group, a poly(lactide-co-glycolide) group or a poly (glycolic acid) group. The X groups may be linear, branched or cyclo groups. Any of the X groups may be directly linked to the d unit (i.e. at the C2 of the monomer unit), or via a functional group such as an amine group, an acyl group, or an amide group, thereby forming linkages that may be represented as X'-ring, X'—NH—, X'—CO-ring, X'CONH-ring, where X' is the hydrophobic group as defined above.

Preferred examples of X groups include those represented by the formulae $CH_3(CH_2)_n$—CO—NH— or $CH_3(CH_2)_n$—NH— or the alkeneoic acid $CH_3$ $(CH_2)_p$—CH=CH—$(CH_2)_q$—CO—NH—, where n is between 4 and 30, and more preferably between 6 and 20, and p and q may be the same or different and are between 4 and 16, and more preferably 4 and 14. A particularly preferred class of X substituents are linked to the chitosan monomer unit via an amide group, for example as represented by the formula $CH_3(CH_2)_n$CO—NH—, where n is between 2 and 28. Examples of amide groups are produced by the coupling of carboxylic acids to the amine group of chitosan. Preferred examples are fatty acid derivatives $CH_3(CH_2)_n$COOH such as those based on capric acid (n=8), lauric acid (n=10), myristic acid (n=12), palmitic acid (n=14), stearic acid (n=16) or arachidic acid (n=18).

In the above formula, $R_1$, $R_2$ and $R_3$ are preferably independently selected from a substituted or unsubstituted alkyl group such as a $C_{1-10}$ alkyl group. $R_1$, $R_2$ and/or $R_3$ may be linear or branched. Preferably, $R_1$, $R_2$ and $R_3$ are independently selected from methyl, ethyl or propyl groups.

In the above formula, $R_8$ and $R_9$ are preferably independently selected from hydrogen and a substituted or unsubstituted alkyl group such as a $C_{1-10}$ alkyl group. $R_8$ and/or $R_9$ may be linear or branched. Preferably, $R_8$ and $R_9$ are independently selected from methyl, ethyl or propyl groups.

In the above formula, $R_4$, $R_5$, $R_6$ and $R_{10}$ present on the C6 or the sugar units are independently selected from hydrogen, a substituted or unsubstituted alkyl group, a substituted or unsubstituted ether group, or a substituted or unsubstituted alkene group. Preferred $R_4$, $R_5$, $R_6$ and $R_{10}$ groups are substituted with one of more hydroxyl groups, or another non-ionic hydrophilic substituent. Examples of $R_4$, $R_5$, $R_6$, and $R_{10}$ groups are represented by the formulae —$(CH_2)_p$—OH, where p is between 1 and 10, and is preferably between 2 and 4, or —$(CH_2)_p$—$CH(CH_2$—$OH)_2$ where p is between 1 and 10 or —$(CH2)_p$—$C(CH_2$—$OH)_r$ where p is between 1 and 10, and r is 3, or —$(CH_2CH_2OH)_p$, where p is between 1 and 300.

The $R_7$ group may be present or absent in the general formula. When absent, it provides a quaternary ammonium functional group that is directly linked to the monomer unit of the chitosan backbone. When the $R_7$ group is present it may be a unsubstituted or substituted alkyl group (e.g. a $C_{1-10}$ alkyl group) for example as represented by the formula —$(CH_2)_n$—, an amine group as represented by the formula —NH—$(CH_2)_n$—, or an amide group as represented by the formula —NH—CO—$(CH_2)_n$—, where n is 1 to 10 and is preferably 1 to 4. A preferred example of the $R_7N^+R_1R_2R_3$ substituent is provided by coupling betaine (—OOC—$CH_2$—$N^+$—$(CH_3)_3$) to the amine substituent of the b unit providing an amide group such as in: —NH—CO—$CH_2$—$N^+R_1R_2R_3$.

As indicated, some of the substituents described herein may be either unsubstituted or substituted with one or more additional substituents as is well known to those skilled in the art. Examples of common substituents include halo; hydroxyl; ether (e.g., $C_{1-7}$ alkoxy); formyl; acyl (e.g. $C_{1-7}$ alkylacyl, $C_{5-20}$ arylacyl); acylhalide; carboxy; ester; acyloxy; amido; acylamido; thioamido; tetrazolyl; amino; nitro; nitroso; azido; cyano; isocyano; cyanato; isocyanato; thiocyano; isothiocyano; sulfhydryl; thioether (e.g., $C_{1-7}$ alkylthio); sulphonic acid; sulfonate; sulphone; sulfonyloxy; sulfinyloxy; sulfamino; sulfonamino; sulfinamino; sulfamyl; sulfonamido; $C_{1-7}$ alkyl (including, e.g., unsubstituted $C_{1-7}$ alkyl, $C_{1-7}$ haloalkyl, $C_{1-7}$ hydroxyalkyl, $C_{1-7}$ carboxyalkyl, $C_{1-7}$ aminoalkyl, $C_{5-20}$ aryl-$C_{1-7}$ alkyl); $C_{3-20}$ heterocyclyl; and $C_{5-20}$ aryl (including, e.g., $C_{5-20}$ carboaryl, $C_{5-20}$ heteroaryl, $C_{1-7}$ alkyl-$C_{5-20}$ aryl and $C_{5-20}$ haloaryl) groups.

The term "ring structure" as used herein, pertains to a closed ring of from 3 to 10 covalently linked atoms, yet more preferably 3 to 8 covalently linked atoms, yet more preferably 5 to 6 covalently linked atoms. A ring may be an alicyclic ring, or aromatic ring. The term "alicyclic ring," as used herein, pertains to a ring which is not an aromatic ring.

The term "carbocyclic ring", as used herein, pertains to a ring wherein all of the ring atoms are carbon atoms.

The term "carboaromatic ring", as used herein, pertains to an aromatic ring wherein all of the ring atoms are carbon atoms.

The term "heterocyclic ring", as used herein, pertains to a ring wherein at least one of the ring atoms is a multivalent ring heteroatom, for example, nitrogen, phosphorus, silicon, oxygen or sulphur, though more commonly nitrogen, oxygen, or sulphur. Preferably, the heterocyclic ring has from 1 to 4 heteroatoms.

The above rings may be part of a "multicyclic group".

Preferably, the amphiphilic carbohydrate compound is quaternary ammonium palmitoyl glycol chitosan (GCPQ). In this case, the palmitoylation level is preferably between 5-50% per monomer. The quaternisation level is preferably between 1-40% per monomer.

In the compositions of the invention the drug is preferably present at a concentration in the range 0.001-1% w/v.

When concentrations are expressed in % w/v, this means the amount of solid, in g, contained in 100 mL of composition.

The amphiphilic carbohydrate compound has a molecular weight in the range 1-50 kDa. Molecular weight is preferably measured using Gel-permeation chromatography-multi-angle light scattering (GPC-MALLS).

The amphiphilic carbohydrate compound is capable of self-assembling into particles in aqueous media without the presence of other agents such as tripolyphosphate. Generally, micelles are formed.

The compositions of the present invention may form particulate aggregates. These may be formed by the aggregation of individual amphiphile molecules and the hydrophilic drug and have a mean particle size of between 10 nm and 20 μm.

Preferably the amphiphilic carbohydrate compound forms nanoparticles which can be loaded with drug. A dispersion of carbohydrate and drug may be formed which is clear or translucent. Generally the amphiphilic compound is mixed with drug and a dispersion is prepared by vortexing and probe sonicating the mixture or by high-pressure homogenisation of the mixture.

The mean particle size can readily be determined microscopically or by using photon correlation spectroscopy and is conveniently determined in aqueous dispersions prior to filtration. More preferably, the polymeric micellar aggregates have a minimum mean particle size of at least 10 nm, and more preferably at least 30 nm, and a maximum mean particle size which is preferably 10 μm or less.

Typically, the ratio of amphiphilic carbohydrate compound to drug is within the range of 1:1 to 50:1, more preferably 1:1 to 20:1.

Typically, the ratio of amphiphilic carbohydrate compound to drug to pharmaceutically acceptable carrier may be about 1-40 mg:1 mg:1 g, for instance 1-5 mg:1 mg:1 g.

The pharmaceutical composition of this invention may be in a liquid or solid form suitable for ocular administration. Generally the formulations are clear or opalescent liquid formulations.

A suitable daily dose can be determined based on age, body weight, administration time, etc. While the daily doses may vary depending on the condition and body weight of the patient, and the nature of the drug, a typical ocular dose is 0.01-10 mg/person/day.

EXAMPLES

Materials and Methods

Polymer

N-palmitoyl-N-monomethyl-N,Ndimethyl-N,N,N-trimethyl-6-O-glycolchitosan (GCPQ) was synthetized and characterized as previously described in I. F. Uchegbu, A. G. Schatzlein, X. Hou, Polymeric micellar clusters and their uses in formulating drugs, in, US20100159014 A1. The GCPQ used for the experiments had 20.51 Mol % of palmitoyl groups per monomer units, 11.93 Mol % of quaternary ammonium groups per monomer units, and a molecular weight of 9.13 KDa.

CsA Compositions

The composition containing CSA was prepared as follows. To a weighed sample of the polymer and weighed sample of the drug was added phosphate buffered saline (pH=7.4, 20 mL). The initial polymer, drug weight ratio was 7.5:1 and the drug content was adjusted to give a concentration of 0.05%, 0.08% and 0.1% w/v. The liquid mixture was vortexed for two minutes to ensure complete mixing and subsequently subjected to high pressure homogenisation (Avestin Emulsiflex, GCT Technology, UK) at 20,000 psi for 30 cycles.

CsA Formulation Stability

For the stability analysis, aliquots of the formulations were stored in triplicate at either: refrigeration temperature (2-3° C.), room temperature (16-22° C.) or at an accelerated temperature (40° C.), and also monitored when subjected to freeze-thaw cycling (−20° C. for 2 days, 5° C. for 2 days and 40° C. for 2 days, repeated for 3 cycles). At various time intervals, formulations were analysed for drug content using a high performance liquid chromatography (HPLC) assay.

CsA Assay

The HPLC assay was performed as previously described in W. P. Cheng, A. I. Gray, L. Tetley, T. L. B. Hang, A. G. Schatzlein, I. F. Uchegbu, Polyelectrolyte nanoparticles with high drug loading enhance the oral uptake of hydrophobic compounds, Biomacromolecules, 7 (2006) 1509-1520. Briefly, aliquots (100 µL) were diluted with an equivalent volume of methanol, the solution filtered (0.22 µm) and the filtrate injected onto a C18 reverse phase onyx monolithic column (100×4.6 mm). The mobile phase was acetonitrile, water (60:40), the flow rate 1.2 mL min-1, the injection volume was 20 µL and the column temperature 70° C. The HPLC system was an Agilent 1200 Series (Agilent Technologies Ltd, UK) and the data was analysed by Agilent ChemStation software.

In Vivo Experiments

For the topical ocular administration of CSA, male New Zeeland rabbits (n=3, Harlan, UK) were dosed with 0.05% w/V CSA composition containing GCPQ and prepared as described above with a minor change to the methodology.

In Vivo Formulation

GCPQ (GCPQLC2Sep13—deprotonated, Mw=13,210 Da, Mn=12,180 Da, Mole % palmitoylation=17%, Mole % quaternary ammonium groups=12%) was dispersed at a concentration of 0.75% w/V in a solution containing 3.1% w/V of glycerine in water. The polymer was allowed to disperse by gently shaking on an orbital shaker for at least 2 hrs. Once the polymer was completely dispersed, the dispersion was filtered using a 3.1 µm syringe filter.

The polymer dispersion above, was added to a weighed amount of CSA powder (the CSA was added at two times the target amount). CSA powder was dispersed by initially vortexing the mixture and, subsequently, by processing for 30 cycles at 18000 psi using a high pressure homogenizer (Avestin C5). After high pressure homogenisation, the pH was adjusted to 7.4 using NaOH (1M). The formulation was stored for at least 24 h at 5° C., it was analysed by HPLC, and finally diluted with a polymer dispersion containing 0.75% w/V of GCPQ and 3.1% w/V of glycerol (previously adjusted to pH 7.4 and filtered using 3.1 µm syringe filters) to make up the formulation to the required strength.

Animal Experiments

New Zealand albino male rabbits between 2.5 and 3 kg (Harlan laboratories, UK) were acclimatised for not less than 5 days before the experiments. The rabbits had free access to water throughout the study. The formulations were administered into both eyes. To administer the formulations, the lower eyelid was gently pulled away from the eyeball and, using a calibrated micropipette, 25 µL of the formulations were applied in the lower conjunctival cul-de-sac. After dosing, the upper and lower eyelids were hand-held together for approximately 5 seconds to permit the formulations to come in contact with the cornea. Subsequently, the number of blinks in the following 60 s was recorded. At prearranged time-points (0.5, 2, 4, 8, 24 hr), a sample of arterial blood was taken from the marginal ear artery. Subsequently the rabbits were culled with an IV over-dose injection of pentobarbital. A tear sample was collected using a 2 µL capillary. The various tissues were dissected, rinsed with 0.9% NaCl solution, dried on a filter paper and stored for subsequently analysis. The eye tissues were harvested in the following order to minimize contamination: (1) aqueous humour, (2) conjunctiva, (3) vitreous humour, (4) lens, (5) cornea and (6) sclera. The tissues coming from both eyes were stored in the same container. Initially (2-5 hrs after dissection) the samples were stored in ice (for 2-5 hours after dissection) and they were subsequently stored at −80° C. until analyses could be performed.

Tissue Analysis

The concentrations of CSA in tissues were determined using liquid chromatography-mass spectrometry (LC-MS/MS).

Preparation of Standards

CSA stock solutions were prepared at a concentration of 1 mg mL$^{-1}$ in glass vials in methanol (for LC-MS, Sigma-Aldrich). Working standards (WS) were prepared by serially diluting the CSA stock solution in methanol to obtain the working standards (Table 1) ranging in concentration from ~50 to 1000000 ng mL$^{-1}$.

TABLE 1

Preparation of CSA working standard solutions

| Code | Dilutions | | Add diluent (µL) | Final concentration CSA (ng/mL) |
|------|-----------|---|------|------|
|      | Take amount (µL) | From | | |
| WS14 | 200 | CsA STD | / | 1000000 |
| WS13 | 100 | WS14 | 100 | 500000 |
| WS12 | 80 | WS13 | 120 | 200000 |
| WS11 | 100 | WS12 | 100 | 100000 |
| WS10 | 100 | WS11 | 100 | 50000 |
| WS9 | 100 | WS10 | 100 | 25000 |
| WS8 | 100 | WS9 | 100 | 12500 |
| WS7 | 100 | WS8 | 100 | 6250 |
| WS6 | 100 | WS7 | 100 | 3125 |
| WS5 | 100 | WS6 | 100 | 1562.50 |
| WS4 | 100 | WS5 | 100 | 781.25 |
| WS3 | 100 | WS4 | 100 | 390.63 |
| WS2 | 100 | WS3 | 100 | 195.31 |
| WS1 | 100 | WS2 | 100 | 97.67 |
| WS0 | 100 | WS1 | 100 | 48.83 |

Diluent: methanol

CsA-d12 (Recipe, Germany) was used as the internal standard. Stock solutions of the internal standard (IS) were prepared at a concentration of 6.25 µg mL$^{-1}$ in acetonitrile. The IS standard solution (IS-PPT) was freshly prepared by diluting the IS stock solution with methanol to yield an IS with a concentration of 5 ng mL$^{-1}$.

Tissues were defrosted (with solid tissue cut into small pieces with scissors) weighed (99.0±1.0 mg or 99 µL for liquid tissues) and placed in 1.5 mL polypropylene microcentrifuge tubes. To each tube was added a volume of the working standards WS0-WS14 (Table 2). Spiked samples were then vortexed for 10 minutes.

TABLE 2

Preparation of CSA calibration standards

| Sample Number | Spike volume (µL) | From | Final concentration (ng/mL) |
|---|---|---|---|
| Std S14 | 1 | WS14 | 10000 |
| Std S13 | 1 | WS13 | 5000 |
| Std S12 | 1 | WS12 | 2000 |
| Std S11 | 1 | WS11 | 1000 |
| Std S10 | 1 | WS10 | 500 |
| Std S9 | 1 | WS9 | 250 |
| Std S8 | 1 | WS8 | 125 |
| Std S7 | 1 | WS7 | 62.5 |
| Std S6 | 1 | WS6 | 31.25 |
| Std S5 | 1 | WS5 | 15.63 |
| Std S4 | 1 | WS4 | 7.81 |
| Std S3 | 1 | WS3 | 3.91 |
| Std S2 | 1 | WS2 | 1.95 |
| Std S1 | 1 | WS1 | 0.97 |
| Std S0 | 1 | WS0 | 0.49 |

Spiked samples were then extracted by adding 400 µL of IS-PPT and vortexed for 4 hours at room temperature. Subsequently the samples were removed from the vortex and left to stand at 5° C. for 30 min before being centrifuged (5000 g×10 minutes). The supernatant was transferred to HPLC vials and analysed using LC-MS.

Sample Preparation

Tissues were defrosted (with solid tissue cut into small pieces with scissors), weighed (100.0±1.0 mg or 100 µL for liquid tissue) and placed in 1.5 mL polypropylene microcentrifuge tubes. Samples were then extracted by adding 400 µL of IS-PPT and vortexed for 4 hours at room temperature. Subsequently the samples were removed from the vortex and left to stand at 5° C. for 30 min before being centrifuged (5000 g×10 minutes). The supernatant was transferred to HPLC vials and analysed using LC-MS.

LC-MS/MS Instrumentation

Samples were analysed over an Agilent 6400 Series Triple Quadrupole LC/MS system (Agilent technologies, Berkshire, UK) comprising a degasser (HiP Degasser 1260/G4225A), a binary pump (HiP 1260 binary pump/G1312B), an autosampler (HiP sampler 1260/G1367E), a column oven (G1316A) and a triple-quadrupole mass spectrometer (G6460A). Agilent MassHunter Workstation Software was used for system control, data acquisition and data processing.

Chromatography Conditions

Samples (injection volume=5 µL) were chromatographed over an Agilent Zorbax Extend-C18 (50×2.1 mm column, pore size=3.5 µm) equipped with a Cartridge Gemini (C18 4×2.0 mm) guard column and at a column temperature of 60° C., with the mobile phase at a flow rate of 600 µL min$^{-1}$. The mobile phase gradient was as shown in Table 3, where Solution A=0.02% w/v Acetic acid in water and Solution B=methanol containing 0.02% w/v acetic acid. Typical retention times for the two analytes, obtained under the above chromatographic conditions, are reported in Table 4.

TABLE 3

Gradient method for LC-MS/MS analyses

| Time (min) | Solution A % | Solution B % |
|---|---|---|
| 0.00 | 30 | 70 |
| 0.01 | 30 | 70 |
| 1.80 | 0 | 100 |
| 2.00 | 0 | 100 |
| 2.10 | 30 | 70 |
| 3.10 | 30 | 70 |

TABLE 4

LC-MS/MS Retention times

| Analyte | Time (min) |
|---|---|
| CSA | 2.14 |
| CSA-d12 | 2.14 |

Mass Spectrometer Conditions

The ion source was an Agilent Jet Stream (AJS) with nitrogen as source, the scan mode was multiple reaction monitoring (MRM), the polarity was in positive ion mode, the nebuliser pressure was at 30 psi, the gas flow was set at 5 L min$^{-1}$, the gas temperature at 340° C., the capillary voltage was set at 5000 V, the sheath gas heater was set at 400° C., the sheath gas flow was set at 11 L min$^{-1}$ and the VCharging was set at 1500 V. Table 5 reports the mass spectrometer condition for the quantification of each of the two analytes.

TABLE 5

Ion channel detector setting for the LC-MS/MS analysis

| Ion Channels | Precursor Ion → Product Ion | MS1/MS2 resolution | Dwell | Fragmentator (V) | Collision Exit Potential (V) | Cell Acceleration Voltage (V) |
|---|---|---|---|---|---|---|
| CSA | 1224.9 → 1112.7 | widest/widest | 370 | 350 | 70 | 1 |
| CSA-d12 | 1236.9 → 1124.2 | widest/widest | 250 | 350 | 75 | 1 |

Quantification

The calibration curves for CSA and CSA-d12 were constructed using the standards prepared as described in Table 2.

Pharmacokinetic Analysis

Microsoft Excel professional plus 2010 was used to calculate pharmacokinetic parameters. IBM SPSS Statistics was used for statistical analyses. Values below the limit of quantification (BLQ) were considered to be 0 for the calculation.

Statistical Analysis

IBM SPSS Statistics was used for statistical analyses. Values below the limit of quantification (BLQ) were considered to be 0 for the calculation. At first, a 2-way ANOVA analysis followed by post-hoc test (Tukey's HSD) was performed to test the difference between the 3 formulations throughout the entire set of time points. When a statistically significant difference was found among the three formulations, statistically significant differences within each time point were evaluated with a one way ANOVA followed by a post-hoc test (either Tukey's HSD or Games-Howell with equal or unequal variance, respectively).

Results

Table 6 reports on the physicochemical characterization of the clear liquid formulations. Osmotic pressure and pH were within the range for ophthalmic preparations.

TABLE 6

Physicochemical properties of the compositions

| Composition | Osmolarity ± SD (mOsm/L) | pH ± SD | [CSA] ± SD (µg/mL) |
|---|---|---|---|
| CSA 0.050% w/V GCPQ 0.375% w/V | 311 ± 1 | 6.8 ± 0.3 | 496.6 ± 61.8 |
| CSA 0.080% w/V GCPQ 0.6% w/V | ND | ND | 717.9 ± 68.0 |
| CSA 0.100% w/V GCPQ 0.750% w/V | 304 ± 1 | 7.0 ± 0.2 | 1020.3 ± 98.0 |

ND: not determined

The formulations were stable with respect to drug content when subjected to the thermal stability study under the conditions stated above (Tables 7-10).

TABLE 7

Drug content for the composition containing CSA 0.050% w/V and GCPQ 0.375% w/V when subjected to the thermal stability study.

| | [CSA] ± SD (µg/mL) | | |
|---|---|---|---|
| Day | Stored at 2-3° C. | Stored at 16-20° C. | Stored at 40° C. |
| 0 | 496.6 ± 61.8 | 496.6 ± 61.8 | 496.6 ± 61.8 |
| 1 | 497.6 ± 68.1 | 471.5 ± 28.2 | 429.9 ± 1.6 |
| 7 | 495.2 ± 34.1 | 568.7 ± 52.4 | 476.2 ± 64.4 |
| 14 | 564.0 ± 32.7 | 544.9 ± 23.7 | 601.2 ± 45.1 |
| 21 | 539.1 ± 26.3 | 496.9 ± 82.7 | 607.3 ± 180.6 |
| 30 | 499.9 ± 54.4 | 467.2 ± 47.0 | 550.1 ± 41.3 |

TABLE 8

Drug content for the composition containing CSA 0.080% w/V and GCPQ 0.600% w/V when subjected to the thermal stability study.

| | [CSA] ± SD (µg/mL) | | |
|---|---|---|---|
| Day | Stored at 2-3° C. | Stored at 16-20° C. | Stored at 40° C. |
| 0 | 717.9 ± 68.0 | 717.9 ± 68.0 | 717.9 ± 68.0 |
| 1 | 795.0 ± 41.2 | 867.1 ± 172.0 | 711.5 ± 125.4 |
| 7 | 636.1 ± 43.4 | 618.1 ± 86.3 | 518.9 ± 1.6 |
| 14 | 803.3 ± 186.7 | 730.0 ± 149.4 | 825.5 ± 193.3 |
| 21 | 679.9 ± 65.7 | 727.2 ± 144.1 | 811.4 ± 125.4 |
| 30 | 736.7 ± 159.6 | 859.1 ± 53.4 | 875.3 ± 270.7 |

TABLE 9

Drug content for the composition containing CSA 0.100% w/V and GCPQ 0.750% w/V when subjected to the thermal stability study.

| | [CSA] ± SD (µg/mL) | | |
|---|---|---|---|
| Day | Stored at 2-3° C. | Stored at 16-20° C. | Stored at 40° C. |
| 0 | 1020.3 ± 98.0 | 1020.3 ± 98.0 | 1020.3 ± 98.0 |
| 1 | 1020.3 ± 98.0 | 1064.8 ± 228.2 | 991.2 ± 78.2 |
| 7 | 1083.3 ± 145.9 | 1042.7 ± 46.3 | 1131.1 ± 204.9 |
| 14 | 979.1 ± 103.8 | 1002.8 ± 100.1 | 1025.5 ± 218.5 |
| 21 | 1070.8 ± 161.8 | 1002.0 ± 94.7 | 1038.2 ± 203.1 |
| 30 | 937.7 ± 58.7 | 883.0 ± 59.8 | 959.5 ± 74.2 |

TABLE 10

Drug content for the composition containing CSA 0.100% w/V and GCPQ 0.750% w/V when subjected to freeze-thaw cycling.

| Storage Days | [CSA] ± SD (µg/mL) | Storage Temperature |
|---|---|---|
| 0 | 782.26 ± 88.21 | Not Applicable |
| 1-2 | 724.85 ± 26.31 | −20° C. |
| 3-4 | 906.99 ± 107.78 | 4° C. |
| 5-6 | 724.31 ± 70.27 | 40° C. |
| 7-8 | 863.16 ± 113.29 | −20° C. |
| 9-10 | 820.26 ± 68.06 | 4° C. |
| 11-12 | 773.26 ± 57.71 | 40° C. |
| 13-14 | 786.46 ± 107.28 | −20° C. |
| 15-16 | 696.72 ± 163.89 | 4° C. |
| 17-18 | 834.18 ± 67.33 | 40° C. |

Formulations presented as opalescent liquids and became reversibly more opaque when subjected to the accelerated storage temperature (40° C.), returned to their opalescent appearance when exposed to a lower (room) temperature and retained their opalescent appearance on storage at lower temperatures (room and refrigeration); this change in appearance on storage at 40° C. is attributed to the change in the intrinsic solubility of cyclosporine A, as the drug becomes less soluble as the temperature rises from refrigeration to human physiological temperatures (solubility=101.5 µg mL−1 at 5° C., 19.9 µg mL−1 at 25° C., and 3.7 µg mL−1 at 37° C.).

There was no drug precipitation observed during the storage period, as determined by visual observation. At all three formulation storage conditions the drug content remained unchanged over the 30 day period (Tables 7-9) (ANOVA test was conducted on the data and there was no significant differences between the initial formulation and the stored formulations).

When subjected to thermal cycling visual macroscopic analysis revealed that the formulations looked slightly cloudy at the end of the 3 cycles, but without any drug precipitation as determined by visual observation. Furthermore the drug content was stable over the thermal cycling period (Table 10) (as determined with an ANOVA test on the results).

The CSA concentration in various tissues after the topical ocular administration of the composition containing CSA 0.050% w/V and GCPQ 0.75% w/v are reported in table 11. Restasis® was administered as a control formulation.

TABLE 11

CSA concentration in various rabbit eye tissues after topical ocular administration of the compositions containing CSA 0.050% w/V and GCPQ 0.75% w/V, and Restasis ®.

| Time (hr) | [CSA] in plasma ± SD (ng/mL) | | [CSA] in conjunctiva ± SD (ng/mg) | | [CSA] in cornea ± SD (ng/mg) | |
|---|---|---|---|---|---|---|
| | GCPQ | Restasis | GCPQ | Restasis | GCPQ | Restasis |
| 0.5 | BLQ_p | BLQ_p | 3864 ± 827 | 608 ± 328 | 1546 ± 653 | 191 ± 31 |
| 2.0 | BLQ_p | BLQ_p | 1182 ± 327 | 528 ± 216 | 1108 ± 391 | 191 ± 48 |
| 4.0 | BLQ_p | 12.93 ± 22.39 | 740 ± 43 | 337 ± 178 | 1328 ± 127 | 170 ± 24 |
| 8.0 | BLQ_p | BLQ_p | 410 ± 44 | 176 ± 51 | 1192 ± 105 | 216 ± 34 |
| 24.0 | BLQ_p | BLQ_p | 95 ± 69 | 83 ± 66 | 846 ± 522 | 197 ± 47 |

| Time (hr) | [CSA] in vitreous humour ± SD (ng/mL) | | [CSA] in aqueous humour ± SD (ng/mL) | | [CSA] in sclera ± SD (ng/mg) | |
|---|---|---|---|---|---|---|
| | GCPQ | Restasis | GCPQ | Restasis | GCPQ | Restasis |
| 0.5 | 54 ± 40 | 11.2 ± 4.6 | 0.7 ± 0.7 | BLQ_a | 627 ± 400 | 93 ± 7.8 |
| 2.0 | 2.5 ± 2.8 | 0.4 ± 0.7 | BLQ_a | BLQ_a | 502 ± 213 | 81 ± 6.9 |
| 4.0 | 5.6 ± 2.5 | 0.4 ± 0.6 | 0.2 ± 0.3 | BLQ_a | 226 ± 24 | 101 ± 36 |
| 8.0 | 4.1 ± 6.2 | 0.6 ± 0.9 | 0.7 ± 0.06 | BLQ_a | 289 ± 84 | 81 ± 23 |
| 24.0 | 7.4 ± 5.8 | 1.3 ± 2.2 | 0.4 ± 0.7 | BLQ_a | 120 ± 52 | 50 ± 33 |

BLQ_p: below limit of quantitation in plasma (1.6 ng/mL);
BLQ_a: below limit of quantitation in aqueous humour (0.5 ng/mL).

The in-vivo topical ocular administration experiment revealed that the composition containing GCPQ was more bioavailable than the commercial composition Restasis® (Table 11). Specifically, drug levels in the cornea and conjunctiva were statistically significantly (p<0.05) higher with the GCPQ composition when compared to Restasis at all time points except the terminal 24 hour time point. Furthermore drug levels in the sclera were statistically significantly (p<0.05) higher with the GCPQ composition when compared to Restasis® at the 4 and 8 hour time points. No differences in drug levels were revealed between the two compositions in the aqueous humour, vitreous humour and plasma.

Taken together these results reveal that the GCPQ composition is more effective in delivering CSA to the eye tissues (cornea and conjunctiva), which are the primary targets for DES. Notably, the CSA concentration in plasma was below the limit of quantitation in plasma (1.6 ng/mL) hence suggesting that the formulation should not induce systemic side effects.

The invention claimed is:

1. A topical ocular formulation comprising an aqueous composition comprising a macrolide immunosuppressant drug selected from sirolimus, cyclosporine A, tacrolimus, and everolimus at a concentration of less than 2% w/v and quaternary ammonium palmitoyl glycol chitosan (GCPQ) at a concentration below 10% w/v, wherein the ratio of the concentration in w/v of GCPQ to the drug is greater than 5:1, and wherein GCPQ has a palmitoylation level between 10 mole % and 40 mole % and a quaternization level between 6 mole % and 20 mole %, wherein the formulation has a pH from 6.5 to 7.4.

2. The formulation according to claim 1, wherein the drug is selected from sirolimus, tacrolimus, and everolimus.

3. The formulation according to claim 1 that does not comprise lipids.

4. The formulation according to claim 1, wherein the drug is encapsulated by self-assembled GCPQ.

5. The formulation according to claim 1, wherein the formulation is in the form of a polymeric aggregate having a mean particle size between 10 nm and 20 μm.

6. The formulation according to claim 1, wherein the macrolide immunosuppressant drug selected from sirolimus, cyclosporine A, tacrolimus, and everolimus is present at a concentration in the range 0.001-1% w/v.

7. A pharmaceutical composition that is a topical ocular formulation comprising one or more pharmaceutically acceptable excipients, a macrolide immunosuppressant drug selected from sirolimus, cyclosporine A, tacrolimus, and everolimus at a concentration of less than 2% w/v, and a quaternary ammonium palmitoyl glycol chitosan (GCPQ) at a concentration of less than 10% w/v, wherein the ratio of the concentration in w/v of GCPQ to the drug is greater than 5:1, and wherein GCPQ has a palmitoylation level between 10 mole % and 40 mole % and a quaternization level between 6 mole % and 20 mole %, wherein the formulation has a pH from 6.5 to 7.4.

8. The pharmaceutical composition according to claim 7, wherein the drug is selected from sirolimus, tacrolimus, and everolimus.

9. The pharmaceutical composition according to claim 7, wherein the composition does not comprise lipids.

10. The pharmaceutical composition according to claim 7, wherein the drug is encapsulated by GCPQ.

11. The pharmaceutical composition according to claim 7, wherein the composition is in the form of a polymeric aggregate having a mean particle size between 10 nm and 20 μm.

12. The pharmaceutical composition according to claim 7, wherein the immunosuppressant drug selected from sirolimus, cyclosporine A, tacrolimus, and everolimus is present at a concentration in the range 0.001-1% w/v.

13. The formulation according to claim 1, wherein the drug is cyclosporine A.

14. The composition according to claim 7, wherein the drug is cyclosporine A.

15. The topical ocular formulation of claim 1, wherein the ratio of the concentration in w/v of GCPQ to the drug is greater than 7.5:1.

16. The topical ocular formulation of claim 1, wherein the macrolide immunosuppressant drug is cyclosporine A at a concentration of 0.05%, 0.08%, or 0.1% w/v.

17. The topical ocular formulation of claim 1, wherein GCPQ has a palmitoylation level between 16 mole % and 32 mole % and the quaternization level between 11 mole % and 19 mole %.

18. The pharmaceutical composition of claim 7, wherein GCPQ has a palmitoylation level between 16 mole % and 32 mole % and the quaternization level between 11 mole % and 19 mole %.

19. The formulation according to claim 1, wherein the drug is tacrolimus.

20. The composition according to claim 7, wherein the drug is tacrolimus.

* * * * *